United States Patent
Kitano et al.

(10) Patent No.: US 11,746,382 B2
(45) Date of Patent: Sep. 5, 2023

(54) METHOD OF DETECTING SOMATIC MUTATIONS IN TUMOR MARKER GENES, AND TUMOR STATUS EVALUATION METHOD

(71) Applicants: TOPPAN PRINTING CO., LTD., Tokyo (JP); NIPPON MEDICAL SCHOOL FOUNDATION, Tokyo (JP)

(72) Inventors: Shiro Kitano, Tokyo (JP); Takeshi Yamada, Tokyo (JP); Goro Takahashi, Tokyo (JP); Takuma Iwai, Tokyo (JP); Koki Takeda, Tokyo (JP)

(73) Assignees: TOPPAN PRINTING CO., LTD., Tokyo (JP); NIPPON MEDICAL SCHOOL FOUNDATION, Tokyo (JP)

( * ) Notice: Subject to any disclaimer, the term of this patent is extended or adjusted under 35 U.S.C. 154(b) by 101 days.

(21) Appl. No.: 16/506,489

(22) Filed: Jul. 9, 2019

(65) Prior Publication Data
US 2019/0330705 A1    Oct. 31, 2019

Related U.S. Application Data

(63) Continuation of application No. PCT/JP2018/000792, filed on Jan. 15, 2018.

(30) Foreign Application Priority Data

Jan. 16, 2017 (JP) ................. 2017-005102

(51) Int. Cl.

| | | |
|---|---|---|
| C07H 21/04 | (2006.01) |
| C12Q 1/68 | (2018.01) |
| C12Q 1/6886 | (2018.01) |
| G16B 40/10 | (2019.01) |
| C12Q 1/6827 | (2018.01) |
| C12Q 1/6851 | (2018.01) |
| C12Q 1/686 | (2018.01) |

(52) U.S. Cl.
CPC .......... *C12Q 1/6886* (2013.01); *C12Q 1/686* (2013.01); *C12Q 1/6827* (2013.01); *C12Q 1/6851* (2013.01); *G16B 40/10* (2019.02)

(58) Field of Classification Search
None
See application file for complete search history.

(56) References Cited

U.S. PATENT DOCUMENTS

2010/0063382 A1    3/2010    Zhou et al.

FOREIGN PATENT DOCUMENTS

| EP | 2 977 464 A1 | 1/2016 |
| JP | 2012-507733 A | 3/2012 |
| WO | WO 2014/148557 A1 | 9/2014 |
| WO | WO 2016/098873 A1 | 6/2016 |

OTHER PUBLICATIONS

Swisher et al. (JAMA Oncology, vol. 2, No. 3, pp. 370-372, Mar. 2016) (Year: 2016).*
Valori et al. (Clin Immunol, vol. 175, pp. 75-81, Dec. 5, 2016). (Year: 2016).*
Smith et al. (Tissue Antigens, vol. 79, pp. 359-366, 2012). (Year: 2012).*
Riedhammer C., Halbritter D., Weissert R. (2014) Peripheral Blood Mononuclear Cells: Isolation, Freezing, Thawing, and Culture. In : Weissert R. (eds) Multiple Sclerosis. Methods in Molecular Biology, vol. 1304. Humana Press, New York, NY. https://doi.org/10.1007/7651_2014_99).*
Gautschi et al. (Cancer Letters, vol. 254, pp. 265-273, 2007).*
Stadler et al. (PLOS, vol. 10, No. 1371, pp. 1-24, Nov. 12, 2015). (Year: 2015).*
Oxnard et al. (Molecular Cancer Ther, Abstract B104, 12_Supplement_2, 2015). (Year: 2015).*
Huang et al. (J. Cancer, vol. 7, No. 13, pp. 1907-1914, 2016) (Year: 2016).*
Gautschi et al. (Cancer Letters, vol. 254, No. 8, pp. 265-273, 2007) (Year: 2007).*
Heidi Schwarzenbach et al., "Cell-free nucleic acids as biomarkers in cancer patients", Nature Review, Jun. 2011, vol. 11, pp. 426-437 +.
Sandra Misale et al., "Emergence of KRAS mutations and acquired resistance to anti-EGFR therapy in colorectal cancer", Nature, 2012, vol. 486(7404), pp. 532-536 +.
Luis A. Diaz Jr. et al., "The molecular evolution of acquired resistance to targeted EGFR blockade in colorectal cancers", Nature, 2012, vol. 486(7404), pp. 537-540 +.
Steven J. Cohen et al., "Relationship of Circulating Tumor Cells to Tumor Response, Progression-Free Survival, and Overall survival in Patients With Metastatic colorectal Cancer", Journal of Clinical Oncology, Jul. 1, 2008, vol. 26(19), pp. 3213-3221 +.
Benjamin J. Hindson et al., "High-Throughput Droplet Digital PCR System for Absolute Quantification of DNA Copy Number", Analytical Chemistry, 2011, vol. 83 (22), pp. 8604-8610 +.
Michael Olivier, "The Invader assay for SNP genotyping", Mutation Research 573, Feb. 10, 2005, pp. 103-110 +.
Dan Y. Wu et al., "The Ligation Amplification Reaction (LAR)—Amplification of Specific DNA Sequences Using Sequential Rounds of Templated-Dependent Ligation", Genomics, vol. 4, 1989, pp. 560-569 +.
Gualberto Ruano et al., "Direct haplotyping of chromosomal segments from multiple heterozygotes via allele-specific PCR amplification" Nucleic Acids Research, 1989, vol. 17, No. 20, p. 8392 +.
C.R. Newton et al., "Analysis of any point mutation in DNA. The amplification refractory mutation system (ARMS)" Nucleic Acids Research, 1989, vol. 17, No. 7, pp. 2503-2516 +.

(Continued)

*Primary Examiner* — Jeanine A Goldberg (57) ABSTRACT

A method of detecting somatic mutations of tumor marker genes includes recovering a peripheral blood mononuclear cell layer from a blood sample collected from a subject and examining whether or not a nucleic acid derived from tumor marker genes having somatic mutations is detected from DNA included in the peripheral blood mononuclear cell layer.

3 Claims, 3 Drawing Sheets

(56) References Cited

OTHER PUBLICATIONS

Masato Orita et al., "Detection of polymorphisms of human DNA by gel electrophoresis as single-strand conformation polymorphisms", Proceedings of the National Academy of Science, USA, Apr. 1989, vol. 86, pp. 2766-2770 +.
Masato Orita et al., "Rapid and Sensitive Detection of Point Mutations and DNA Polymorphisms Using the Polymerase Chain Reaction", Genomics, Aug. 1, 1989, vol. 5, pp. 874-879 +.
Elizabeth M. Swisher et al., "Somatic Mosaic Mutations in PPM1D and TP53 in the Blood of Women With Ovarian Carcinoma" JAMA Oncol., Mar. 1, 2016, vol. 2, No. 3, pp. 370-372 (12 pages) **.
International Search Report dated Apr. 17, 2018 in corresponding International Patent Application No. PCT/JP2018/000792 (2 pages).
Written Opinion of the International Searching Authority dated Apr. 17, 2019 in corresponding International Patent Application No. PCT/JP2018/000792 (6 pages).
J. Zhu et al.; "Expression and significance of myeloid differentiation factor 88 in non-small cell lung carcinoma and normal paracancerous tissues"; Department of Lung Tumor, Sichuan Tumor Hospital; DOI http://dx.doi.org/10.4238/2015.November.13.7; Genetics and Molecular Research, vol. 14, No. 4: p. 14239-14245 (2015); 7 pages.
Leslie K. Diaz et al.; "CD44 Expression is Associated with Increased Survival in Node-Negative Invasive Breast Carcinoma"; Clin Cancer Res 2005; vol. 11, No. 9, May 1, 2005: p. 3309-3314 (downloaded from clincancerres.aacrjournals.org on Dec. 20, 2021); 7 pages.
Notice of Reasons for Rejection dated Nov. 16, 2021 in Japanese Patent Application No. 2018-561442.
Cristina Gutierrez et al., "KRAS mutational status analysis of peripheral blood isolated circulating tumor cells in metastatic colorectal patients"; Oncology Letters, vol. 6, 2013, 1343-1345, DOI: 10.3892/ol.2013.1544; (3 pages).
Notice of Reasons for Rejection dated Mar. 1, 2022 in Japanese Patent Application No. 2018-561442 (3 pages) (5 pages English Translation).

* cited by examiner

METHOD OF DETECTING SOMATIC MUTATIONS IN TUMOR MARKER GENES, AND TUMOR STATUS EVALUATION METHOD

CROSS REFERENCE TO RELATED APPLICATIONS

This application is a continuation application based on a PCT Patent Application No. PCT/JP2018/000792, filed Jan. 15, 2018, whose priority is claimed on Japanese Patent Application No. 2017-005102, filed on Jan. 16, 2017, the entire contents of which are hereby incorporated by reference.

BACKGROUND OF THE INVENTION

Field of the Invention

The present invention relates to a method of relatively non-invasively detecting the presence or absence of somatic mutations in tumor marker genes in tumor tissues and a tumor status evaluation method.

Priority is claimed on Japanese Patent Application No. 2017-005102, filed on Jan. 16, 2017, the content of which is incorporated herein by reference.

Description of Related Art

As predictive factor of therapeutic effects of an anti-cancer agent, somatic mutations in cancer genes involved in signal transfer have drawn attention. For example, as predictive factors of therapeutic effects of cetuximab or panitumumab, which is an anti-EGFR (epidermal growth factor receptor) antibody drug which is a molecular target drug in colorectal cancer therapy, RAS gene mutations are exemplified. In addition, as predictive factors of therapeutic effects of molecular target drugs of low-molecular compounds such as gefitinib and erlotinib in lung cancer therapy, point mutations or deficiency of EGFR are exemplified. In addition, as predictive factors of the efficacy of imatinib in leukemia, BCR-ABL fusion genes, EML4-ALK fusion genes in EGFR-negative lung cancer patients, or the like have also been examined in actual clinical settings.

For prediction of therapeutic effects of a molecular therapeutic drug, in general, somatic mutations in tumor tissues are used as an index, and thus genotypes of cancer genes in tumor tissue samples collected by biopsy are examined. In addition, since somatic mutations can occur at any time, it is desirable to chronologically monitor somatic mutations as a predictive factor of the therapeutic effect, and to understand the cancer status in real time. However, a majority of patients receiving chemotherapy have tumors in deep sites of the body such as the lung and liver. For this reason, biopsies from these sites are extremely large invasions for patients, and it is difficult to perform chronological biopsy.

In recent years, it has been reported that cancer patients have a larger amount of cell-free (cf) DNA in blood than healthy persons, and the cfDNA amount in blood can be expected to be a tumor marker (for example, refer to Schwarzenbach, et al., Nature Review, 2011, vol. 11, p. 426-437). In addition, it has been reported that the presence or absence of drug resistance acquisition of an anti-EGFR antibody drug for colorectal cancer can be also correlated with somatic mutations of KRAS genes of cfDNA in blood, similar to somatic mutations of KRAS genes in tumor tissues. That is, it has also been reported that the tumor status can be understood by detecting somatic mutations of KRAS genes in cfDNA in blood (for example, refer to PCT International Publication No. WO2014/148557 and Misale, et al., Nature, 2012, vol. 486 (7404), p. 532-536 and Diaz, et al., Nature, 2012, vol. 486 (7404), p. 537-540). Even in a case where it is difficult to repeat biopsy in general biopsy, it becomes possible to monitor somatic mutations by using blood as a proxy sample of the tissues.

However, a cfDNA amount in blood serum or blood plasma is approximately $10^3$ copies, which is an extremely small amount, and a proportion of allele of tumor marker genes therein is also as small as approximately 0.1%. For this reason, even in cancer patients in which somatic mutations in tumor marker genes are detected in primary lesion tissues, the somatic mutations are not necessarily detected from cfDNA. In addition, although it has already been reported that CTC (peripheral blood circulating tumor cells, peripheral blood circulating cancer cells) and the like are included in peripheral blood, and there is a correlation between the number of CTC and prognosis of the patient, detection frequency of CTC greatly varies depending on the cancer type and the detection technology. For example, an average number of CTC that is detected from stage IV colorectal cancer patients by cell search of J & J Corporation, authorized by FDA, is only five (for example, refer to Cohen, et al., JOURNAL OF CLINICAL ONCOLOGY, 2008, vol. 26 (19), p. 3213-3221). Thus, liquid biopsy targeting relatively non-invasively collectable body fluid samples such as blood is a biopsy which allows understanding of the real-time status while reducing the burden on cancer patients, but in order to perform detection of somatic mutations in tumor marker genes by liquid biopsy, it is required to sufficiently increase detection accuracy.

SUMMARY OF THE INVENTION

Technical Problem

An object of the present invention is to provide a method of detecting the presence or absence of somatic mutations in tumor marker genes in tumor tissues from a blood sample with accuracy and a tumor status evaluation method.

Solution to Problem

The present inventors found that it is possible to detect somatic mutations in tumor marker genes in tumor tissues of a subject with high accuracy by using not DNA in blood plasma or blood serum but DNA of a peripheral blood mononuclear cell layer (PBMC layer) as provision samples, thereby completing the present invention.

A method of detecting somatic mutations in tumor marker genes according to a first aspect of the present invention includes recovering a peripheral blood mononuclear cell layer from a blood sample collected from a subject, and examining whether or not a nucleic acid derived from tumor marker genes having somatic mutations is detected from DNA included in the peripheral blood mononuclear cell layer.

In the first aspect, in some cases, the subject is receiving surgical excisional treatment on tumor sites or anti-tumor therapy at a time of collection of the blood sample, or has received surgical excisional treatment on tumor sites or anti-tumor therapy before the time of collection of the blood sample.

In the first aspect, in some cases, recovering the peripheral blood mononuclear cell layer from the blood sample may be performed by Ficoll density gradient centrifugation.

In the first aspect, in some cases, the nucleic acid derived from tumor marker genes having somatic mutations may be detected by a real-time PCR method, a digital PCR method, a next-generation sequencer method, or an electrochemical detection method.

In the first aspect, in some cases, the tumor marker genes may be KRAS genes.

A tumor status evaluation method according to a second aspect of the present invention includes examining, whether or not the nucleic acid derived from tumor marker genes having somatic mutations is detected from DNA included in the peripheral blood mononuclear cell layer of the subject by the method of detecting somatic mutations in tumor marker genes according to the first aspect, and evaluating the presence or absence of onset or relapse of tumors, or susceptibility to a molecular target drug, of the subject, based on the detection result of the nucleic acid derived from tumor marker genes having somatic mutations.

In some cases, the tumor status evaluation method according to the second aspect may further includes evaluating that the tumors of the subject have no susceptibility to the molecular target drug targeting the tumor marker encoded by the tumor marker genes, or have a high possibility of having acquired resistance against the molecular target drug in a case where the nucleic acid derived from tumor marker genes having somatic mutations is detected from DNA included in the peripheral blood mononuclear cell layer of the subject.

In some cases, the tumor status evaluation method according to the second aspect may further includes evaluating that there is a high possibility that tumor recurrence or new metastasis has occurred in the subject in a case where the subject has received surgical excisional treatment on tumor sites or anti-tumor therapy with respect to a primary lesion having somatic mutations included in tumor marker genes in the past, and the nucleic acid derived from the tumor marker genes having somatic mutations is detected from DNA included in the peripheral blood mononuclear cell layer of the subject In the second aspect, in some cases, the nucleic acid derived from the tumor marker genes having somatic mutations may not be detected from DNA included in blood plasma or blood serum recovered from the blood sample, or peripheral blood circulating cancer cells may not be detected from the blood sample.

In the second aspect, in some cases, the tumor marker genes may be KRAS genes, and the molecular target drug may be an EGFR inhibitor.

In the second aspect, in some cases, the tumor may be metastatic myeloblastoma, gastrointestinal interstitial tumor, elevated skin fibrosarcoma, colon cancer, colorectal cancer, lung cancer, non-small cell lung cancer, small cell lung cancer, chronic myeloproliferative disease, acute myeloid leukemia, thyroid cancer, pancreatic cancer, bladder cancer, kidney cancer, melanoma, breast cancer, prostate cancer, ovarian cancer, cervical cancer, head and neck cancer, brain tumor, hepatocellular carcinoma, hematologic malignancy, or precancer that causes these cancers.

Advantageous Effects of Invention

It is possible to detect the presence or absence of somatic mutations in tumor marker genes in tumor tissues of cancer patients with high sensitivity from a relatively low-invasive blood sample by the method of detecting somatic mutations in tumor marker genes according to the aspects of the present invention. For this reason, it is possible to evaluate tumor status of cancer patients, particularly, a possibility of relapse of tumors or efficacy of a molecular target drug relatively non-invasively with high accuracy without requiring invasive examination with a large burden such as biopsy, by the tumor status evaluation method according to the aspects of the present invention using the detection method.

DETAILED DESCRIPTION OF THE INVENTION

<Method of Detecting Somatic Mutations in Tumor Marker Genes>

A method of detecting somatic mutations in tumor marker genes according to a first embodiment of the present invention (hereinafter, sometimes referred to as "detection method according to the present invention") uses DNA of a PBMC layer as a provision sample for detecting somatic mutations in tumor marker genes. By using DNA of the PBMC layer, it is possible to detect somatic mutations in tumor marker genes in cfDNA with higher sensitivity than in a case of using DNA included in blood serum or blood plasma. The detection method according to the present embodiment specifically includes a recovery step of recovering a PBMC layer from a blood sample collected from a subject and a mutation detection step of examining whether or not a nucleic acid derived from tumor marker genes having somatic mutations is detected from DNA included in the recovered PBMC layer.

In general, when detecting somatic mutations in tumor marker genes in cfDNA, in order to prevent deterioration of detection sensitivity of a nucleic acid derived from mutant-type genes due to mixing of normal DNA derived from leukocytes, that is, a nucleic acid derived from wild-type genes, gene mutations are detected from DNA in blood serum or blood plasma from which corpuscle components have been removed. In addition, a buffy coat layer is used for CTC detection and the like, but the buffy coat layer includes a large amount of corpuscle components, similar to the PBMC layer. Therefore, the buffy coat layer is not used for searching for somatic mutations in tumor marker genes in cfDNA. Similarly, although leukocyte components are removed, the PBMC layer includes a considerably large amount of mononuclear cell components such as lymphocytes, and thus is generally not selected for a gene analysis sample of a general liquid biopsy. Contrary to the finding in the related art that the PBMC layer including a large amount of DNA derived from corpuscles is not suitable for detection of somatic mutations, the present inventors demonstrate that it is possible to detect somatic mutations with higher sensitivity by using DNA of the PBMC layer, compared to a case of using DNA of blood serum or blood plasma.

The tumor marker genes are genes of which the expression amount in tumor tissues is remarkably different in a patient group (cancer patient group) in which tumors develop and a group in which tumors do not develop such as a healthy person group. The tumor marker genes used in the present embodiment may be genes of which the expression amount is less in the cancer patient group than in the healthy person group, but may be preferably genes of which the expression amount is greater in the cancer patient group than in the healthy person group. Among these, since the tumor marker genes used in the present embodiment are classified into wild-type and mutant-type which causes somatic mutations and a preferable therapeutic method in anti-tumor treatment differs by the genotype, tumor marker genes for which differentiation of the genotype of the tumor tissues of the cancer patient is clinically required are preferable. Examples of such tumor marker genes include RAS genes, EGFR genes, BCR-ABL fusion genes, EML4-ALK fusion genes, and the like.

In the detection method according to the present embodiment, it is particularly preferable to detect somatic mutations in the KRAS genes.

A method of recovering the PBMC layer from the blood sample collected from a subject is not particularly limited, and can be used by being appropriately selected from known methods used for separating the PBMC layer from blood. As a method of separating the PBMC layer from the blood, for example, Ficoll density gradient centrifugation, a method of using a "BD Vacutainer CPT Cell Preparation Tube" (manufactured by Nippon Becton Dickinson Co., Ltd.), and the like are exemplified. These methods can be performed by a conventional method. As Ficoll, for example, a reagent manufactured by GE Healthcare Japan Co., Ltd. can be used. In the Ficoll density gradient centrifugation, centrifugal separation treatment is performed by adding Ficoll to a blood sample. In this manner, the PBMC layer is formed by being sandwiched between a Ficoll layer and a blood plasma/blood serum layer.

Subsequently, DNA included in the recovered PBMC layer is extracted, and it is detected whether or not a nucleic acid derived from tumor marker genes having somatic mutations is included in the DNA. Extraction of DNA from the PBMC layer can be performed by a conventional method. In addition, detection of a nucleic acid derived from tumor marker genes in DNA extracted from the PBMC layer or determination of the genotype of the detected nucleic acid derived from tumor marker genes can be performed by a conventional method. As the nucleic acid derived from tumor marker genes, a full length or a portion thereof of genome DNA of tumor marker genes, or an amplification product obtained by artificially amplifying thereof by polymerase chain reaction (PCR), and the like are exemplified.

Detection of a nucleic acid derived from tumor marker genes can be, for example, performed by a real-time PCR method, a digital PCR method, a next-generation sequencer method, an electrochemical detection method, or the like. The electrochemical detection method is a convenient method with the highest versatility in DNA measurement.

For detection of a nucleic acid derived from tumor marker genes in DNA extracted from the PBMC layer in the present embodiment, the real-time PCR method and the digital PCR method are preferable from the viewpoint that quantitative detection of DNA can be performed with high sensitivity. In addition, using the same theory as that of the digital PCR, a method of quantification of a DNA amount using a next-generation sequencer can be also used for detection of a nucleic acid derived from tumor marker genes. However, since there is a concern that DNA in the PBMC layer is fragmented similar to DNA in blood serum or blood plasma, it is preferable to design a primer such that a PCR product length is approximately 100 to 200 bp, or equal to or less than 100 bp.

For example, the presence or the status (genotype) of the nucleic acid derived from tumor marker genes in DNA extracted from the PBMC layer can be determined by detecting using digital PCR. In particular, it is possible to perform detection with high sensitivity by using a technique of droplet digital PCR (ddPCR) of Bio-Rad (Hindson, et. al., Analytical Chemistry, 2011, vol. 83 (22), pp. 8604-8610) or by using a digital PCR apparatus "RainDrop Digital PCR System" of Raindance Technologies. The greater the number of droplets, the higher the analysis accuracy becomes. In order to ensure performance of detecting 0.01% of mutations, 10,000 droplets are required to detect one mutant. In order to ensure sufficient detection sensitivity, it is preferable to define a surfactant concentration in a master mixture of PCR. For example, ethylene glycol or glycerol used as a preservative solution such as DNA extension enzyme preferably has a final concentration of equal to or less than 0.15%, or Triton-X preferably has a final concentration of equal to or less than 0.0003%. When the surfactant has this final concentration or higher, an emulsion number is sharply decreased, and it becomes difficult to detect a PCR product with high sensitivity. In this case, gene portions to be amplified can be optionally selected from any of a non-gene region and a gene region.

In addition, by PCR using nucleic acids and nucleic acid fragments extracted from the PBMC layer as templates, an absolute amount of allele copy number of tumor marker genes which are expected to be included in the nucleic acids is increased, and then diluted to approximately $10^6$ copy number, and thus it is also preferable to perform a known mutation detection method. In addition, the method may be combined with the digital PCR.

Examples of other methods include a method of amplifying a DNA fragment of a region including somatic mutations in tumor marker genes by real-time PCR using nucleic acids extracted from a PBMC layer as a template and the like, bringing a probe capable of being specifically hybridized to the genotype of targeted somatic mutations detected with respect to the obtained amplified product into contact, and detecting whether or not an association has been formed with high sensitivity.

The probe is detectably labeled with radioactive isotopes ($^3$H, $^{32}$P, $^{33}$P, and the like), fluorescent agents (rhodamine, fluorescein, and the like), or chromogenic agents, for example. In addition, the probe may be an antisense oligomer, for example, PNA, morpholino-phosphoramidates, and LNA. A base length of the probe is approximately 8 nucleotides to approximately 100 nucleotides, preferably approximately 10 nucleotides to approximately 75 nucleotides, more preferably approximately 15 nucleotides to approximately 50 nucleotides, and further more preferably approximately 20 nucleotides to approximately 30 nucleotides.

The presence or the status of the nucleic acid derived from tumor marker genes in the PBMC layer can be analyzed using an invader method (Michael Olivier, Mutation Research 573: 103-110, 2005). In the invader method, an allele probe and an invader oligo are hybridized so as to partially form a three-dimensional bases on a double-stranded DNA prepared by PCR and the like or mRNA. Here, a part of a 5' end of the allele probe is designed to have a non-complementary sequence (flap portion) with the double-stranded DNA or mRNA, but the invader oligo has a completely complementary sequence therewith. Two kinds of allele probes are respectively designed to be complementary with a wild-type and a mutant-type, competitively hybridized to the double-stranded DNA or mRNA, and when completely complementarily hybridized, a flap endonuclease identifies parts of the three-dimensional bases, and a flap portion of the allele probe is hybridized with a self-complementary FRET cassette existing in the same reaction system. At this time, the part of three-dimensional bases is formed, the flap endonuclease cuts a targeted mutation, and fluorescence-modified DNA fragments in the FRET cassette are released and separated from a quenching substance in the FRET. Then, the fluorescence-modified DNA fragments emit fluorescence. Theoretically, the flap portion of the cut allele probe can be re-hybridized to another FRET cassette, and thus it is a technique in which a signal is amplified and mutations can be detected with extremely high sensitivity.

Ligase chain reaction which is known in the field can be used to amplify a fragment including a region encoding mutation sites of tumor marker genes (for example, refer to Wu, et. al., Genomics, 1989, vol. 4, refer to pp. 560-569). In addition, a technique known as allele-specific PCR can be used (for example, refer to Ruano and Kidd, Nucleic Acids Research, 1989, vol. 17, pp. 8392). According to the technique, a primer that is hybridized to somatic mutations of a specific tumor marker gene at the 3' end is used. In a case where a specific somatic mutation does not exist, an amplification product is not observed. In addition, Amplification Refractory Mutation System (ARMS) (for example, refer to Newton et. al., Nucleic Acids Research, 1989, vol. 17, pp. 7) can also be used.

For detection of a nucleic acid derived from tumor marker genes in the PBMC layer, or determination of the genotype of a nucleic acid derived from the detected tumor marker genes, other methods used in a case of detecting gene mutations or in a case of detecting insertion and deletion of genes can also be used. As the method, specifically, for example, a method of using a sequence analysis method based on the Sanger method, and directly determining a base sequence of genome DNA or mRNA of tumor marker genes in the PBMC layer, or amplification products thereof is exemplified. In addition, determination of a base sequence can also be performed via PCR. Furthermore, it is possible to use a restriction fragment length polymorphic (RFLP) probe with respect to genes or marker genes therearound to score modification or insertion of alleles in the polymorphic fragment. In addition, it is also possible to use single-stranded DNA conformational polymorphic (SSCP) analysis to detect a base change variant of an allele (Orita et. al., Proceedings of the National Academy of Sciences, USA, 1989, vol. 86, pp. 2766-2770, and Genomics, 1989, vol. 5, pp. 874-879).

By making a reagent used to detect a nucleic acid derived from tumor marker genes in the nucleic acids extracted from the PBMC layer into a kit, it is possible to more conveniently perform the detection method according to the present embodiment. The kit may include documents in which protocols regarding detection of a nucleic acid derived from tumor marker genes in the PBMC layer or the genotype determination method are described, a reagent and the like for recovering the PBMC layer from a blood sample such as Ficoll.

The blood sample used in the detection method according to the present embodiment may be collected from any subject, but the subject is preferably a subject in which the onset of tumor is suspected, a subject in which a cancer has developed at the time of collection of the blood sample or before that, or a subject who has been definitively diagnosed to have developed cancer. Among these, a patient who has received surgical excisional treatment on tumor sites or anti-tumor therapy at a time of collection of the blood sample, or a patient who has received surgical excisional treatment on tumor sites or anti-tumor therapy before the time of collection of the blood sample is more preferable.

<Tumor Status Evaluation Method>

In the tumor status evaluation method according to the first embodiment of the present invention (hereinafter, referred to as "evaluation method according to the present invention"), it is examined by a detection method according to the embodiment of the present invention whether or not a nucleic acid derived from tumor marker genes having somatic mutations is detected from DNA included in the PBMC layer of a subject (examination step), and the presence or absence of onset or relapse of a tumor or susceptibility to a molecular target drug for the subject is evaluated based on the detection result (evaluation step).

In addition, in the tumor status evaluation method according to the present embodiment, before or after the examination step, it may be examined whether or not the nucleic acid derived from tumor marker genes having somatic mutations is detected from DNA included in blood plasma or blood serum recovered from the blood sample (blood plasma blood serum detection step). In this case, the nucleic acid derived from tumor marker genes having somatic mutations may not be detected from the DNA included in the blood plasma or blood serum recovered from the blood sample.

In addition, in the tumor status evaluation method according to the present embodiment, before or after the examination step, it may be examined whether or not peripheral blood circulating cancer cells are detected from the blood sample (peripheral blood circulating cancer cell detection step). In this case, peripheral blood circulating cancer cells may not be detected from the blood sample. In addition, these steps may be performed in parallel with the examination step.

In many tumor patients, the amount of nucleic acids derived from tumor marker genes derived from tumor tissues in cfDNA is small. For this reason, from the viewpoint of detection sensitivity, even when the genotype of the tumor marker genes in tumor tissues is a somatic mutant-type, there are many cases where a nucleic acid derived from somatic mutant-type tumor marker genes cannot be detected from DNA in the blood serum or the blood plasma. On the contrary, in the detection method according to the present embodiment, it is possible to detect tumor tissues which exist in the body of the subject, and of which tumor marker genes have a somatic mutant-type from blood that can be low-invasively collected with high sensitivity. That is, based on the detection result of the detection method according to the embodiment of the present invention, it is possible to evaluate a possibility that tumor tissues of which the tumor marker genes are the somatic mutant-type are present in the body of the subject with high accuracy. As shown in Examples to be described below, in a cancer patient having tumor tissues of which tumor marker genes are the somatic mutant-type, even in a case where only a nucleic acid derived from wild-type tumor marker genes can be detected from nucleic acids in the blood plasma or in a case where CTC is not detected from the blood, there is a case where a nucleic acid derived from the same mutant-type tumor marker genes as that of the tumor tissues can be detected from the nucleic acids of the PBMC layer.

For example, in a case where a nucleic acid derived from tumor marker genes having somatic mutations is detected from the nucleic acids included in the PBMC layer of a subject, it is evaluated that there is a high possibility that tumor tissues of which the tumor marker genes are the somatic mutant-type exist in the body of the subject. In contrast, in a case where a nucleic acid derived from tumor marker genes having somatic mutations is not detected from the nucleic acids included in the PBMC layer of the subject, it is evaluated that there is a low possibility that tumor tissues of which the tumor marker genes are the somatic mutant-type exist in the body of the subject.

In a case where the subject did not receive definitive diagnosis of cancer in the past, or in a case where the subject has received surgical excisional treatment on tumor sites with respect to a primary lesion, it can be evaluated that there is a high possibility that tumor develops in a case where a nucleic acid derived from tumor marker genes having somatic mutations is detected. In addition, in a subject who was in remission due to anti-tumor therapy, in a case where a nucleic acid derived from tumor marker genes having somatic mutations is detected, it can be evaluated that there is a high possibility that tumors revive, that is, metastasis or recurrence has occurred.

In a cancer patient after tumor excision, it is important to perform prompt detection and perform an appropriate therapy in a case where recurrence or metastasis has occurred. For this reason, regular examination is performed regarding the presence or absence of recurrence or metastasis. At this time, from the viewpoint of invasiveness with respect to the subject, cost, or the like, in clinical practice, computed tomography (CT) is rarely used at high frequency, and a method of monitoring general tumor markers such as CEA and CA-19 is used. However, there is a case where an abnormal value is not shown from these tumor markers even if tumors exist. In addition, there is a problem in that the result of a healthy person or a patient having a disease other than tumors may often exceed a standard value, and the reliability level is low.

On the contrary, in the evaluation method according to the present embodiment, since detection of a nucleic acid derived from tumor marker genes having somatic mutations from nucleic acids included in the PBMC layer is performed, the evaluation method imparts less burden and cost to the patient than CT, is appropriate for monitoring, is excellent in detection sensitivity, and allows evaluation with higher reliability. For this reason, the evaluation method according to the present embodiment is particularly preferably performed on the blood sample collected from a patient who is receiving surgical excisional treatment on tumor sites or anti-tumor therapy at a time of collection of the blood sample, or has received surgical excisional treatment on tumor sites or anti-tumor therapy before the time of collection of the blood sample. By performing the method on the blood sample collected from the cancer patient, regarding the presence or absence of recurrence or metastasis of tumors, or the presence or absence of introduction of somatic mutations in tumor tissues, evaluation with relatively higher reliability can be expected, compared to a case of evaluation only based on specific tumor markers such as CEA and CA-19. In general, in cancer therapy, blood collection for tumor marker examination is performed at a frequency of approximately once a month. Here, it is possible to chronologically perform the evaluation method according to the present embodiment using residues of the blood sample of tumor marker examination.

In a case where the blood sample used in the present embodiment was collected from a subject who is receiving surgical excisional treatment on tumor sites or anti-tumor therapy or a subject who has received surgical excisional treatment on tumor sites or anti-tumor therapy before blood collection, the kind of tumors of the subject are not particularly limited. In addition, the tumors may be primary tumors, may be metastatic tumors, or may be recurrent tumors. In addition, the tumors may be present at a plurality of locations in the body of the subject. The tumors include brain cancer, liver cancer, kidney cancer, bladder cancer, breast cancer, gastric cancer, ovarian cancer, colon cancer, prostate cancer, pancreas cancer, lung cancer, vulvar cancer, thyroid cancer, esophageal cancer, and sarcoma, glioblastoma, head and neck cancer, leukemia and lymphoid malignancies. More specifically, the tumors include neuroblastoma, intestinal cancer (for example, rectal cancer, colorectal cancer, familial colorectal polyposis cancer and hereditary non-polyposis colorectal cancer), esophageal cancer, lip cancer, larynx cancer, hypopharynx cancer, tongue cancer, salivary gland carcinoma, gastric carcinoma, adenocarcinoma, medullary thyroid cancer, thyroid artery papillary cancer, kidney cancer, renal parenchyma cancer, ovarian cancer, cervical cancer, endometrial cancer, endometrial cancer, choriocarcinoma, pancreatic cancer, prostate cancer, testicular cancer, breast cancer, urinary tract cancer, melanoma, brain tumor (for example, glioblastoma, astrocytoma, meningioma, medulloblastoma, and peripheral neuroectodermal tumors), Hodgkin's lymphoma, non-Hodgkin's lymphoma, bar kit lymphoma, acute lymphocytic leukemia (ALL), chronic lymphocytic leukemia (CLL), acute myeloid leukemia bone (AML), chronic marrow leukemia (CML), adult T-cell leukemia, hepatocellular carcinoma, gall bladder carcinoma, bronchial carcinoma, small cell lung cancer, non-small cell lung cancer, multiple myeloma, basal cell carcinoma, teratoma, retinoblastoma, choroidal melanoma, seminoma, rhabdomyosarcoma, craniopharyngioma (craniopharyngeoma), osteosarcoma, chondrosarcoma, leiomyosarcoma, liposarcoma, fibrosarcoma, and Ewing's sarcoma, and plasmacytoma.

As excised tumors of the subject from which the blood sample used in the present embodiment is collected, metastatic medulloblastoma, gastrointestinal stromal tumors, dermatofibrosarcoma protuberans, colon cancer, colorectal cancer, lung cancer, non-small cell lung cancer, small cell lung cancer, chronic myeloproliferative disease, acute myelogenous leukemia, thyroid cancer, pancreatic cancer, bladder cancer, kidney cancer, melanoma, breast cancer, prostate cancer, ovarian cancer, cervical cancer, head and neck cancer, brain tumor, hepatocellular carcinoma, hematologic malignancies, or precancer causing these cancers are preferable, and colorectal cancer, colon cancer, lung cancer, hepatocellular carcinoma, breast cancer, ovarian cancer, prostate cancer, renal cancer, head and neck cancer, or cervical cancer are more preferable.

In a case where the blood sample used in the present embodiment is collected from a subject who is receiving surgical excisional treatment on tumor sites or anti-tumor therapy, or a subject who has received surgical excisional treatment on tumor sites or anti-tumor therapy before collection of blood, the anti-tumor therapy that the subject receives is not particularly limited. Specifically, chemotherapy, radiation therapy, and the like are exemplified. Chemotherapy and radiation therapy may be combined.

A chemotherapeutic agent used in chemotherapy is not particularly limited, but may be a compound having cytotoxicity or cytostaticity. Specifically, the chemotherapeutic agent includes (i) anti-metabolite, for example, fluorouracil, capecitabine, cytarabine, fludarabine, 5-fluoro-2'-deoxyuridine, tegafur gimeracil oteracil potassium (TS-1), gemcitabine, hydroxyurea, or methotrexate; (ii) DNA fragmentation agent, for example, bleomycin; (iii) DNA-crosslinking agent, for example, chlorambucil, cisplatin, cyclophosphamide, or nitrogen mustard; (iv) intercalating agent, for example, adriamycin (doxorubicin) or mitoxantrone; (v) protein synthesis inhibitor, for example, L-asparaginase, cycloheximide, puromycin, or diphtheria toxin; (vi) topoisomerase I toxin, for example, camptothecin, or topotecan; (vii) topoisomerase 11 toxin, for example, etoposide (VP-16), or teniposide; (viii) microtubule-associated agent, for example, colcemid, colchicine, paclitaxel, vinblastine, or vincristine; (ix) kinase inhibitor, for example, flavopiridol, staurosporine, STI571 (CPG57148B), or UCN-01 (7-hydroxy staurosporine); (x) various investigational drugs, for example, thioplatin, PS-341, phenylbutyrate, ET-18-OCH3, or farnesyl transferase inhibitors (L-739749, L-744832); polyphenols, for example, quercetin, resveratrol, piceatannol, epigallocatechin gallate, theaflavins, flavanols, procyanidines, beturinic acid, and derivatives thereof; (xi) hormones, for example, glucocorticoid or fenretinide; and (xii) anti-hormones, for example, tamoxifen, finasteride, or LHRH antagonists. In addition, the chemotherapeutic agent also includes folinic acid (leukoborin), oxaliplatin, Illinoethecan, daunarubicin, taxotail, and mitomycin C. In addition, the chemotherapeutic agent also includes a molecular target drug such as cetuximab, panitumumab, bebashidzumabu, gefitinib, erlotinib, regorafenib, crizotinib, sunitinib, sorafenib, everolimus, trastuzumab, lapatinib, and rituximab. Only one kind of these chemotherapeutic agents may be used, or two or more thereof may be used in combination. In the evaluation method according to the present embodiment, in a case where the subject from whom the blood sample is collected has received chemotherapy at the time of collection of blood or before the blood collection, the chemotherapy is preferably chemotherapy using one or more chemotherapeutic agents selected from fluorouracil, leucovorin, oxaliplatin, capecitabine, tegafur gimeracil oteracil potassium, irinotecan, bevacizumab, ceruximab, and panitumumab.

In the evaluation method according to the present embodiment, the tumor marker genes to be a target for detecting somatic mutations are preferably genes for which differentiation of the genotype of the tumor tissues is clinically required since a preferable therapeutic method in anti-tumor treatment differs by the genotype of the tumor tissues, which is preferably RAS genes, EGFR genes, BCR-ABL fusion genes, or EML4-ALK fusion genes, and more preferably KRAS genes. In addition, in the evaluation method according to the present embodiment, it is preferable to evaluate susceptibility to a molecular target drug targeting tumor markers encoded by the used tumor marker genes based on the detection result of somatic mutations in the tumor marker genes.

For example, KRAS gene mutations are used as a predictor of the therapeutic effect of EGFR inhibitors, and administration of different kinds of molecular target drugs is recommended for cancer patients with tumor tissues of which KRAS genes are the wild-type and cancer patients with tumor tissues of which KRAS genes are the somatic mutant-type. For example, with respect to an EGFR inhibitor such as cetuximab (also known as antibody 225), tumor tissues of which KRAS genes are the wild-type have susceptibility, but tumor tissues of which KRAS genes are the somatic mutant-type have no susceptibility. For this reason, in general, cetuximab is administered to a cancer patient whose KRAS genes are the wild-type, and for a cancer patient whose KRAS genes are the somatic mutant-type, other molecular target drugs such as panitumumab are selected. Therefore, when the evaluation method according to the present embodiment is performed using the KRAS genes as tumor marker genes, it is possible to detect the genotype of the KRAS genes of tumor tissues in the body of the subject with higher reliability. Further, it is possible to evaluate susceptibility of tumor tissues in the body of the subject with respect to the molecular target drug targeting KRAS and efficacy in a case of administering the molecular target drug, with high accuracy, based on the detection result. As a result, it is possible to select a therapeutic method appropriate for the subject by the evaluation result. That is, evaluation obtained by the evaluation method according to the present embodiment is clinically extremely useful for predicting the therapeutic effect of chemotherapeutic agents.

For heterogeneity of cancer, even if there exist somatic mutations of tumor marker genes in the primary lesion, there are not always the same mutations in the metastatic lesion. In fact, in colorectal cancer, a mutation consistency rate of KRAS genes in the primary lesion and the metastatic lesion (liver) is only about 90%, and in 10% of patients, the metastatic lesion has no susceptibility to cetuximab used in the primary lesion, and is not efficacious. For this reason, it is important to promptly detect the genotype of tumor marker genes of the metastatic lesion and to evaluate the presence or absence of relapse of tumors of the subject and susceptibility of the molecular target drug based on the detection result.

In addition, as somatic mutations of the tumor marker genes occur in tumor tissues, susceptibility to the molecular target drug is changed in some cases. For example, there is a case where even in tumor tissues in which the wild-type KRAS genes are initially expressed, somatic mutations occur, and resistance against the EGFR inhibitor such as cetuximab is acquired. Therefore, after acquisition of resistance, in order to promptly switch to other molecular target drugs, it is also important to chronologically perform the evaluation method according to the present embodiment on cancer patients, to detect the genotype of tumor tissues, and to monitor the possibility of acquiring resistance against a molecular target agent targeting tumor markers encoded by tumor marker genes.

For example, in the examination step, in a case where a nucleic acid derived from tumor marker genes having somatic mutations is detected from the nucleic acids included in the PBMC layer of a subject, it is evaluated that there is a high possibility that tumors in the body of the subject have no susceptibility to a molecular target agent targeting tumor markers encoded by the tumor marker genes or have acquired resistance against the molecular target agent. On the contrary, in a case where a nucleic acid derived from tumor marker genes having somatic mutations is not detected in the nucleic acids included in the PBMC layer of the subject, it is evaluated that there is a high possibility that tumors in the body of the subject have susceptibility to the molecular target agent targeting tumor markers encoded by the tumor marker genes or have not acquired resistance against the molecular target agent.

For example, in a case of a subject who received surgical excisional treatment on tumor sites or anti-tumor therapy with respect to a primary lesion in which the tumor marker genes have somatic mutations in the past, in the examination step, when a nucleic acid derived from the tumor marker genes having somatic mutations is detected from DNA included in the PBMC layer of the subject, it is evaluated that there is a high possibility that tumor recurrence or new metastasis has occurred. On the contrary, when a nucleic acid derived from the tumor marker genes having somatic mutations was not detected from DNA included in the PBMC layer of the subject, it is evaluated that there is a low possibility that tumor recurrence or new metastasis has occurred in the subject.

EXAMPLES

Hereinafter, the present invention will be described in detail with reference to examples, but the present invention is not limited to the examples. The following tests have been approved by the Ethics Committee of the Nippon Medical School Hospital, and informed consent including the present study was obtained from all patients.

Example 1

From nucleic acids of PBMC layers of three recurrent colorectal cancer patients (patients A to C), it was examined whether or not a nucleic acid derived from somatic mutant-type KRAS genes was detected.

(Clinical Sample)

6 to 9 mL of peripheral blood of three recurrent colorectal cancer patients (patients A to C) who had already had an excision of the primary lesions and had new metastatic lesions (liver) was collected before or after surgical excisional surgery on the metastatic lesions. The date of blood collection of the patient A was Jul. 29, 2015, and the date of blood collection of the patients B and C was Jul. 22, 2015, and operations from PBMC separation to gene mutation detection were performed on the same date.

The patient A was diagnosed with ascending colon cancer and metastatic liver tumor on May 23, 2014, started mFOLFOX6 chemotherapy (fluorouracil, folinic acid, and oxaliplatin) on Jun. 12, 2014, and received combination therapy of FOLFOX chemotherapy (fluorouracil, folinic acid, and oxaliplatin) and bevacizumab from Jul. 19, 2014 to Oct. 23, 2015. As a result of CT, in the patient A, an increase in tumor tissues in liver metastatic lesion was confirmed on Jul. 28, 2015, which is a date before the date of blood collection (not illustrated).

The patient B received surgery of surgically excising rectal cancer (stage Ill) on Nov. 4, 2009, received mFOLFOX6 chemotherapy (20 courses) from Nov. 30, 2009 to Sep. 24, 2009, and started chemotherapy (oral administration) using both of TS-1 and PSK from Oct. 27, 2010. Multiple lung metastases were identified on Apr. 27, 2012, combination therapy of mFOLFOX6 chemotherapy and bevacizumab (biweekly administration) was performed from Jun. 27, 2012 to Mar. 30, 2014, FOLFIRI chemotherapy was received from May 14, 2014 to Dec. 29, 2015, and combination therapy of irinotecan and TS-1 from Jan. 6, 2016 to May 29, 2016. As a result of CT, in the patient B, SD (stabilization of disease) was held on May 27, 2015 before the date of blood collection, but progress of disease was confirmed on Aug. 10, 2016.

The patient C received surgery of rectal cancer on Jan. 18, 2011. In addition, with respect to simultaneous liver metastasis, combination therapy of FOLFOX chemotherapy and panitumumab (biweekly administration) was performed. After that, the patient C received partial excision surgery of the liver with respect to liver metastasis on May 2, 2012, and combination therapy of FOLFOX chemotherapy and cetuximab (biweekly administration) was performed from Dec. 5, 2012 to Apr. 16, 2015. After that, since resistance against cetuximab was acquired, combination therapy of FOLFIRI chemotherapy and bevacizumab was performed from May 13, 2015. As a result of CT, in the patient C, any of SD (stabilization of disease) was held on Jul. 1, 2015.

Separation of PBMC from Peripheral Blood

For recurrent colorectal cancer patients (patients A to C), separation of the PBMC layer from a portion of peripheral blood by Ficoll density gradient centrifugation was performed by the following procedure. A method of subjecting all blood samples to Ficoll density gradient centrifugation is the most commonly used method in separation of monocyte cells.

More specifically, first, after whole blood samples were dispensed into blood collection tubes, whole blood was diluted at 1:1 with a PBS buffer in a class II safety cabinet. Subsequently, a 50 mL plastic tube to which Ficoll was introduced was fixed at a certain angle, and the diluted whole blood samples were carefully laminated on Ficoll. The tube was centrifuged at 20° C. for 20 minutes at 833×g (2,125 rpm) (Thermo Scientific Sorvall X1R was used). At this time, acceleration of a centrifugal separator was set at a maximum of "9", and deceleration was performed at "0" (no brake). By centrifugation, PBMC was laminated between a Ficoll layer and a blood plasma layer. While holding the laminated state, the tube was taken from the centrifugal separator, and the PBMC layer between the Ficoll layer and the blood plasma layer was carefully removed, and dispensed into a new 15 mL plastic tube. After adding a PBS buffer to the 15 mL tube and washing cells in the PBMC layer, the 15 mL tube was set in a centrifugal separator, and centrifuged at 425×g (1,518 rpm) for 10 minutes (acceleration and deceleration are respectively in 9 stages). After that, a supernatant was discarded, the cells were washed with the PBS buffer again, a supernatant was discarded, and the cells were suspended in an appropriate amount of PBS buffer. The prepared suspension was set as preparation PBMCs.

(Purification of DNA from Preparation PBMCs)

DNA was extracted from the obtained preparation PBMCs and purified. Extraction and purification of DNA were performed using QIAamp (registered trademark) DNA Mini (manufactured by Qiagen) kit according to instructions included in the kit.

In addition, a DNA concentration in the preparation PBMCs was fluorescence-measured using a commercially available kit (product name: Qubit2.0, manufactured by Life Technologies Inc.), and the DNA concentration was calculated.

(Separation of Blood Plasma from Peripheral Blood)

Each portions of peripheral blood collected from three colorectal cancer patients (A to C) was centrifuged (1,500 rpm, 10 minutes). After the obtained crude blood plasma component was further centrifuged (1,500 rpm, 10 minutes), a supernatant portion from which a cell fragment was removed was recovered, and this was set as a blood plasma sample.

(Isolation and Purification of cfDNA from Blood Plasma Sample)

Isolation and purification of cfDNA from blood plasma was performed using a QIAamp Circulating Nucleic Acid Kit (manufactured by Qiagen) according to instructions included in the kit. An amount of preparation blood plasma used in the kit was set to be 1 mL, and a final elution from a spin column was performed using 50 µL of a TE buffer.

(Quantification of cfDNA)

Quantification of cfDNA was performed using a Qubit (registered trademark.) Fluorometer (manufactured by Life Technologies, Inc.). All samples to be measured were used by diluting the isolated DNA to 200-fold with a predetermined reaction solution.

(Detection and quantification of KRAS gene mutations by digital PCR)

Somatic mutations of KRAS genes in DNA extracted and purified from preparation PBMCs and a blood plasma sample of each patient were detected by a QUANTSTUDIO (registered trademark) 3D digital PCR system. For detection, a probe labeled with FAM (registered trademark) was used as a probe capable of being specifically hybridized with an allele of KRAS mutant-type (G12V), and a probe labeled with VIC (registered trademark) was used as a probe capable of being specifically hybridized with an allele of KRAS wild-type. In addition, although not illustrated, detection of KRAS mutant-type (G12D) was also similarly performed.

Figure 1:
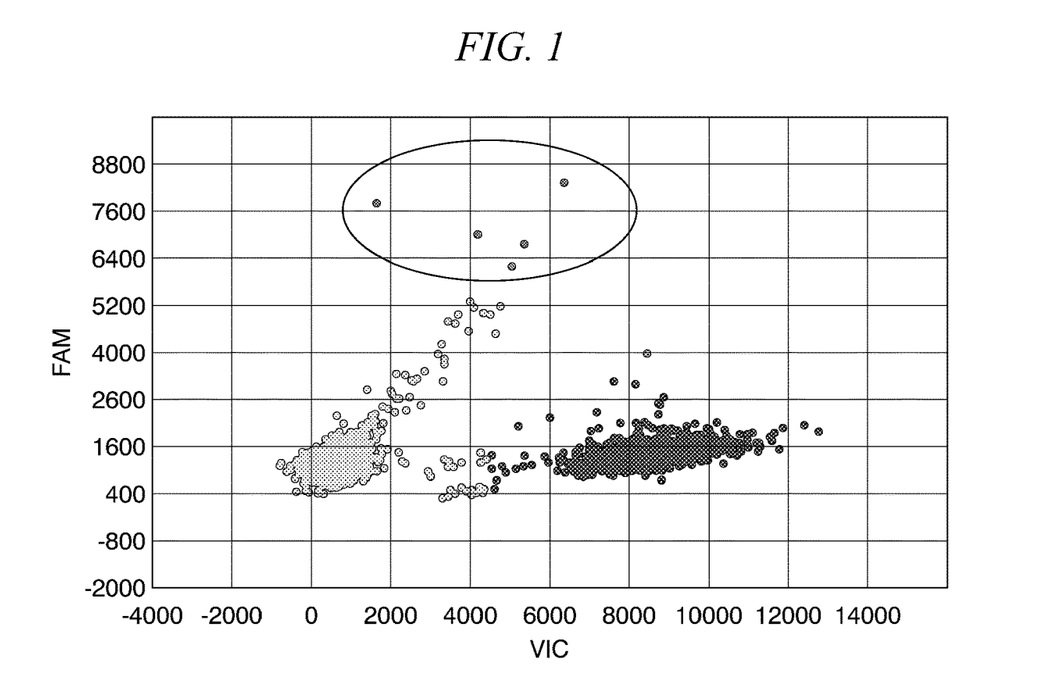
FIG. 1 is a diagram illustrating a digital PCR result of DNA (KRAS_G12V), FAM: KRAS mutant-type (G12V), and VIC: KRAS wild-type in PBMC of a patient A in Example 1.
Figure 2:
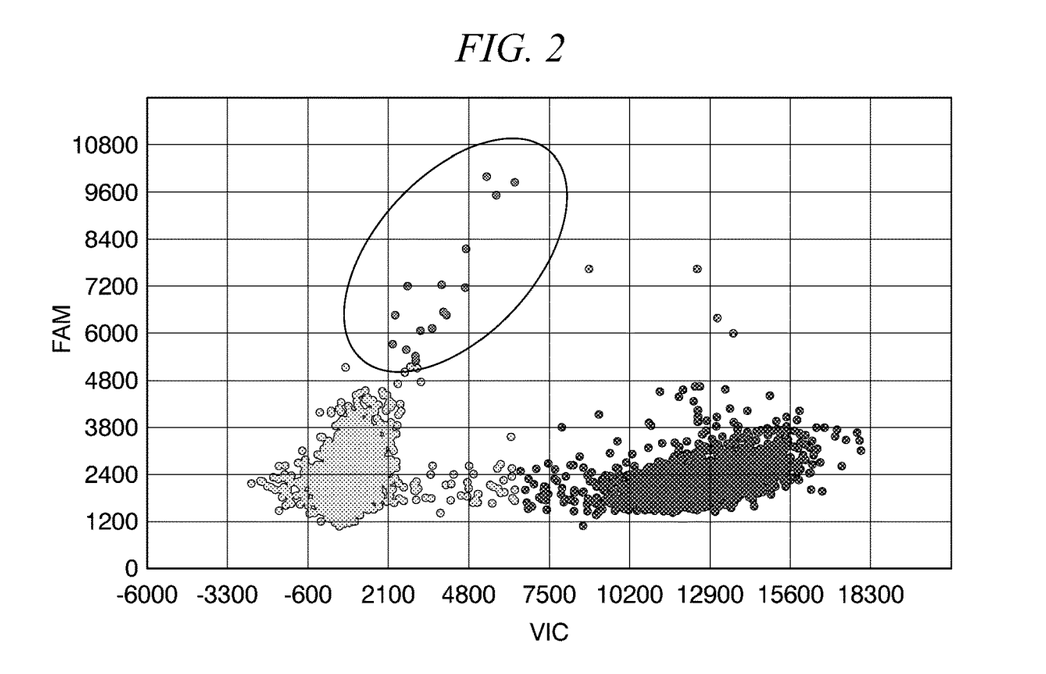
FIG. 2 is a diagram illustrating a digital PCR result of DNA (KRAS_G12V), FAM: KRAS mutant-type (G12V), and VIC: KRAS wild-type in PBMC of a patient B in Example 1.
Figure 3:
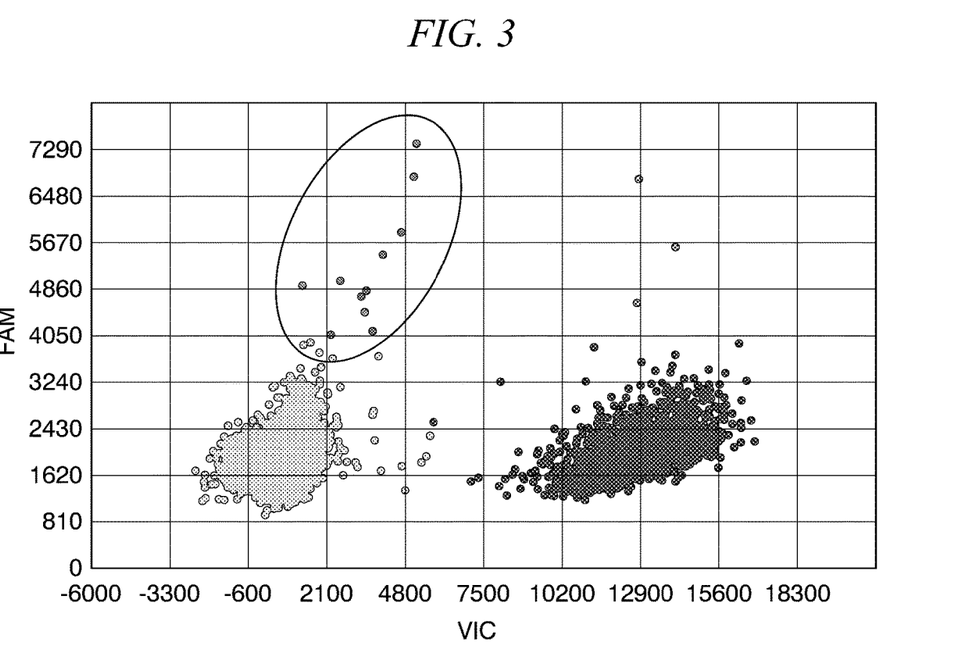
FIG. 3 is a diagram illustrating a digital PCR result of DNA (KRAS_G12V), FAM: KRAS mutant-type (G12V), and VIC: KRAS wild-type in PBMC of a patient C in Example 1.

FIGS. 1 to 3 illustrate the digital PCR results for DNA in PBMCs of the patients A to C.

In the figures, the vertical axis represents fluorescence intensity of FAM, and the horizontal axis represents fluorescence intensity of VIC.

In the figures, dots of the circled region are dots representing detection of somatic Mutations of KRAS Genes.

(Measurement of CEA and CA19-9 in Blood Plasma)

CA19-9 and CEA in the blood plasma were measured by a CLEIA method (chemiluminescence enzyme immunoassay). A standard value of CA19-9 was equal to or less than 37 U/mL, and a standard value of CEA was equal to or less than 5.0 ng/mL.

Figure 4:
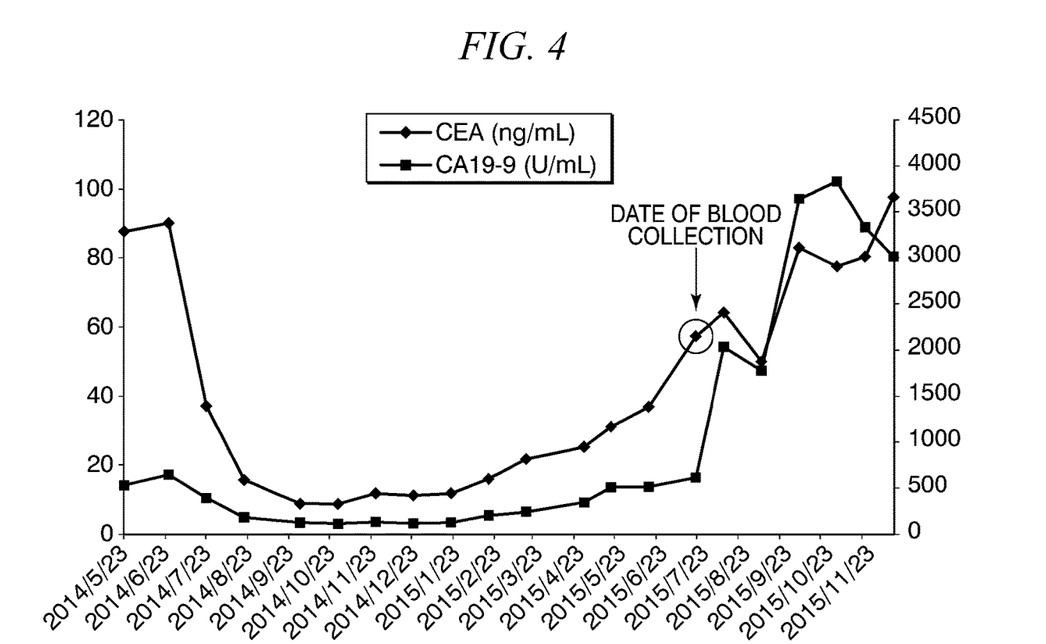
FIG. 4 is a diagram illustrating chronological changes in concentrations of CEA and CA19-9 in blood plasma of the patient A in Example 1.
Figure 5:
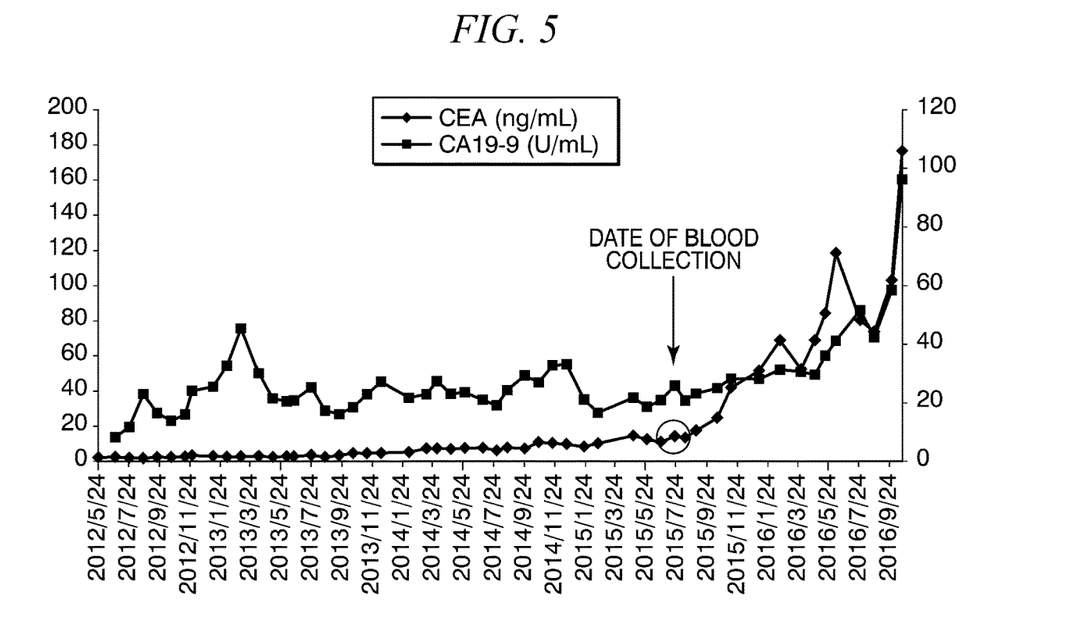
FIG. 5 is a diagram illustrating chronological changes in concentrations of CEA and CA19-9 in blood plasma of the patient B in Example 1.
Figure 6:
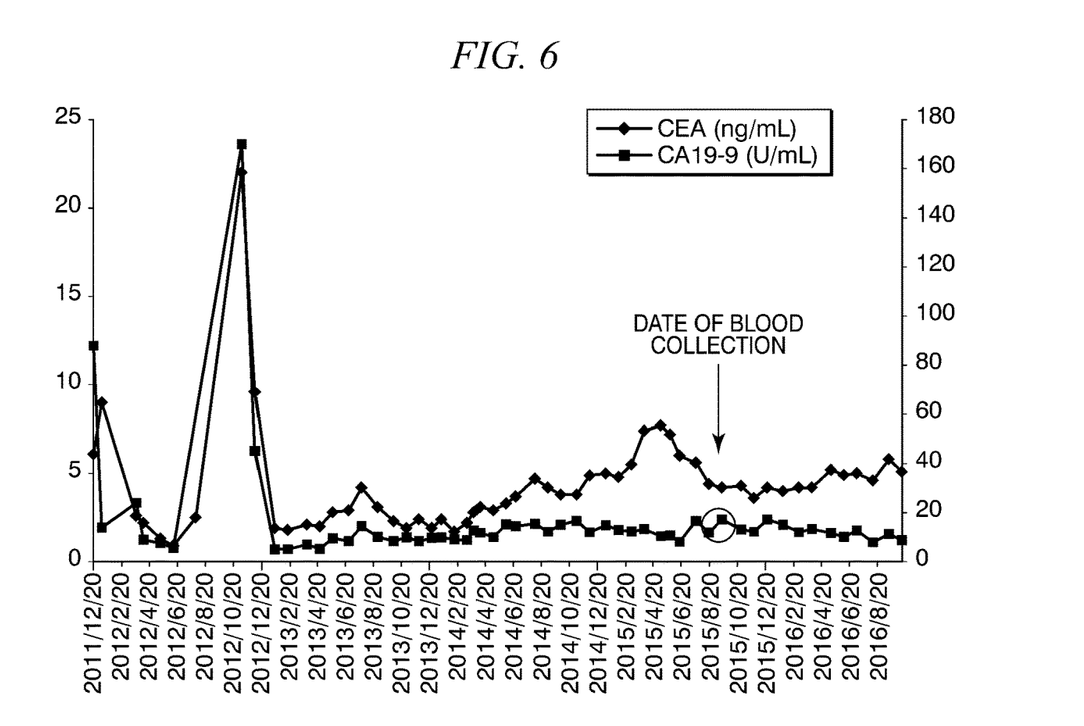
FIG. 6 is a diagram illustrating chronological changes in concentrations of CEA and CA19-9 in blood plasma of the patient C in Example 1.

FIGS. 4 to 6 illustrate measurement results of CEA concentrations and CA19-9 concentrations in the blood plasma of patients A to C. In the figures, the right axis represents CEA concentration (ng/mL), and the left axis represents CA19-9 concentration (U/mL).

Measurement of Number of CTC

Using a CTC concentration recovery apparatus (product name: "ClearCell FX System", manufactured by ClearBridge Ltd.), the number of CTC was measured using 7.5 mL of peripheral blood of the patients A to C.

None of CTC was detected from the peripheral blood of all the three patients A to C.

(Isolation and Purification of DNA from FFPE Slice)

As a tissue specimen collected from metastatic lesions and primary lesions of patients A to C, DNA isolation was performed also from formalin-fixed paraffin-embedded slices (FFPE slices) thereof. DNA isolation and purification from FFPE slices was performed using the QIAamp DNA FFPE Tissue Kit (manufactured by Qiagen) according to the instructions included in the kit. Using three pieces of FFPE slices sliced into 10 µm per sample, DNA extracted therefrom was eluted in 100 µL of a TE buffer.

(Direct Sequencing)

Base sequence analysis of a nucleic acid derived from KRAS genes included in DNA extracted from the FFPE slices as surgical specimens of the primary lesion and the metastatic lesion and a nucleic acid derived from KRAS genes in the blood plasma collected before or after surgical excisional surgery of primary lesions, was performed by direct sequencing. More specifically, cycle sequencing by a big dye terminator method was performed by a conventional method using a primer specific to a base sequence of KRAS genes.

Table 1 shows the number of copies and a ratio (%) of somatic mutations per unit volume of KRAS gene in DNA extracted and purified from the preparation PBMCs of the patients A to C by digital PCR. In DNA on the PBMC layers of the patients A to C, nucleic acids derived from somatic mutant-type KRAS genes were detected. The number of copies or the ratio of somatic mutations of KRAS genes included in the PBMC layers varied by the patient. Since a detectable limit of the QUANTSTUDIO (registered trademark) 3D digital PCR system was 0.1%, and within a detection range of an analysis apparatus in all three cases, it was found that KRAS gene mutations were detectable from the PBMC layers of the cancer patients.

TABLE 1

|  | Patient A | Patient B | Patient C |
| --- | --- | --- | --- |
| Number of DNA copies (copy/µL) | 122.2 | 251.0 | 246.6 |
| Ratio of mutations (%) | 0.327 | 0.579 | 0.125 |

In addition, the detection result of the genotype of KRAS genes included in DNA extracted from tissue slices of a primary lesion and a metastatic lesion of each patient and a nucleic acid derived from somatic mutant-type KRAS genes from DNA (cfDNA) of the blood plasma and DNA of the PBMC layer is shown in Table 2. In Table 2, "WT" means that a nucleic acid derived from somatic mutant-type KRAS genes was not detected, and "-" means that the genotype was not examined without acquiring a tissue slice of the metastatic lesion.

TABLE 2

|  | Blood plasma | PBMC layer | Metastatic lesion | Primary lesion |
| --- | --- | --- | --- | --- |
| Patient A | WT | G12V | — | G12V |
| Patient B | WT | G12D, G12V | G12D, G12V | G12V |
| Patient C | WT | G12V | — | WT |

As a result, in all three cases, all of mutant-type KRAS genes were detected in DNA of the PBMC layer, whereas only wild-type KRAS genes were detected in DNA (cfDNA) in the blood plasma. In particular, in the patient B from whom the genotype of the metastatic lesion could be confirmed, both of the two mutant-types (G12D and G12V) of the metastatic lesion were detected also from DNA of the PBMC layer. Hence, it was confirmed that somatic mutant-type KRAS genes which are the same as those of the metastatic lesion could be detected from the nucleic acid of the PBMC layer. In addition, in the patient C, at a time when the metastatic lesion was confirmed, cetuximab was administered, but at a time when the genotype was measured from DNA of the PBMC layer, drug resistance was acquired and thus administration was switched to administration of bevacizumab. Therefore, similar to the genotype of the PBMC layer, there is an extremely high possibility that the metastatic lesion is also the somatic mutant-type of G12V. For this reason, it was apparent that also from the result of the patient C, DNA of the PBMC layer greater reflects the genotype of tumor tissues than DNA of the blood plasma, and by setting DNA of the PBMC layer as a provision sample, it is possible to detect the genotype of tumor marker genes of tumor tissues with higher sensitivity. The genotype of the metastatic lesion of the patient A was not able to be checked, but somatic mutations detected from DNA of the PBMC layer had the same genotype (G12V) as that of the primary lesion layer. Therefore, there is a high possibility that the genotype of the metastatic lesion is also the mutant-type of G12V similar to that of the primary lesion or the PBMC layer. In addition, as illustrated in FIGS. 4 to 6, even in a case where concentrations in blood of CEA and CA19-9 of the patients were not stable, according to the tumor status evaluation method of the present invention, it is possible to obtain a stable result of tumor status, and it is also possible to specify the mutant-type of tumor marker genes of tumor tissues.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method of detecting a somatic mutation in a tumor marker gene, comprising:
    a) examining in blood plasma or blood serum recovered from a blood sample whether or not the tumor marker gene has a somatic mutation in DNA, the blood sample collected from a colorectal cancer patient;
    b) confirming that the tumor marker gene somatic mutation is not detected;
    c) recovering a peripheral blood mononuclear cell layer from the blood sample by Ficoll density gradient centrifugation; and
    d) detecting from the peripheral blood mononuclear cell layer, after the confirming, the presence of the somatic mutation in the DNA from the tumor marker gene;
    wherein the tumor marker gene is KRAS,
    wherein the method of detecting is selected from the group consisting of a real-time PCR method, a digital PCR method and an electrochemical method.

2. The method according to claim 1,
    wherein the subject is receiving surgical excisional treatment on a tumor site of the subject or anti-tumor therapy at a time of collection of the blood sample, or has received the surgical excisional treatment on the tumor site or the anti-tumor therapy before the time of collection of the blood sample.

3. A method for detecting recurrence of cancer using a somatic mutation in a tumor marker gene, comprising:
    a) examining in blood plasma or blood serum recovered from a blood sample whether or not the tumor marker gene has a somatic mutation in DNA, the blood sample being collected from a lung or liver cancer patient;
    b) confirming that the tumor marker gene somatic mutation is not detected;
    c) recovering a peripheral blood mononuclear cell layer from the blood sample by Ficoll density gradient centrifugation; and
    whether or not the tumor marker gene has a somatic mutation in the DNA, the blood sample
    d) detecting from the peripheral blood mononuclear cell layer, after the confirming, the presence of the somatic mutation in the DNA from the tumor marker gene extracted,
    wherein the method of detecting is selected from the group consisting of a real-time PCR method, a digital PCR method and an electrochemical method.

* * * * *